United States Patent [19]
Minton

[11] Patent Number: 5,210,894
[45] Date of Patent: May 18, 1993

[54] PILLOW FOR SUPPORTING THE HEAD OF A HALO WEARING USER

[76] Inventor: Trilby M. Minton, 132 Loxley Dr., Columbus, Ohio 43207

[21] Appl. No.: 978,352

[22] Filed: Nov. 18, 1992

[51] Int. Cl.⁵ ............................................. A47G 9/00
[52] U.S. Cl. ............................................. 5/637; 5/636
[58] Field of Search ................... 5/636, 637, 638, 639, 5/622; 297/391; D6/601

[56] References Cited

U.S. PATENT DOCUMENTS

| | | |
|---|---|---|
| D. 256,728 | 9/1980 | Allen ........................................ 5/636 |
| 3,757,365 | 9/1973 | Kretchmer . |
| 4,259,757 | 4/1981 | Watson . |
| 4,550,458 | 11/1985 | Fiore .................................... 297/393 |
| 4,710,991 | 12/1987 | Wilmore et al. ........................ 5/638 |
| 4,752,064 | 6/1988 | Voss ........................................ 5/638 |
| 4,903,690 | 2/1990 | Campbell ............................. 128/68 |
| 5,018,231 | 5/1991 | Wang . |

Primary Examiner—Alexander Grosz
Attorney, Agent, or Firm—Thomas S. Baker, Jr.

[57] ABSTRACT

A pillow for use by the user of a head immobilizing device having a circular member and a plurality of longitudinally extending struts which pillow has a T-shaped slot which will accommodate said device while allowing unslotted portion to support the user's head.

6 Claims, 1 Drawing Sheet

PILLOW FOR SUPPORTING THE HEAD OF A HALO WEARING USER

FIELD OF THE INVENTION

The instant invention relates to a pillow which supports the head and neck of a person wearing a halo head immobilizer apparatus when they are sleeping.

BACKGROUND OF THE INVENTION

A halo is an orthopedic device used to provide stability and rigidity to the neck and head of a person who is recovering from neurological surgery, most commonly a spinal fusion, necessitated because of an extreme injury to the neck, in most cases where a fracture to the neck has been sustained. The halo provides the stability by immobilizing the head and neck, effectively preventing any movement, either from side to side or from front to back, of the head and neck. The halo is attached to the person during the reparative surgery via four titanium screws, which are placed into the first layer of the skull. Made of a combination of metals, most frequently titanium and graphite, the halo weighs upward to 15 pounds, although this figure may vary depending on the combination of metals used in its construction. The halo is further attached to a vest worn by a person, said vest being constructed of durable plastic and being lined with either lambswool or synthetic wool padding. An adjustment means is provided at the side and bottom edges of the vest to enable the wearer to adjust the vest to an appropriate circumference for his/her waist and to allow for the placement of clothing underneath the vest. Typically, a person utilizing this device wears the halo from six to nine months, in order to allow for the full complete healing of a surgically repaired spine, although this length of time may vary depending on the severity of the initial injury and on the recuperative process specific to the individual.

During the convalescence of the patient, and given the severe nature of the injury initially necessitating the surgery, it is extremely difficult for the patient to sleep or rest while wearing the halo. No currently available pillow provides comfortable and appropriate support for the head of the halo wearer. While lying in either the supine or side position, the halo interferes with conventional and customary sleeping positions by preventing the head of a wearer from being supported by a pillow. A conventional pillow engages the halo frame and barely touches the head of a wearer. Thus, even while sleeping the wearer's head is supported by the screws and the halo frame which is not comfortable. Furthermore, the weight of the halo, in addition to its inflexibility, makes it extremely difficult for the wearer to sit for any significant period of time without suffering from stress and tiredness of the shoulders.

It thus becomes desirable to provide a pillow which simultaneously will accommodate the structure of a halo and will properly support the head and neck of a wearer to enable a recovering neurosurgical patient to sleep and rest comfortably during the convalescent period. Such a pillow also can prevent further stress to the injured region, and to the shoulders and chest of the person, while sleeping. Such a device may also serve to relieve the stress caused by a person's movement while awake, and may be used to support the head and neck while in a sitting position when the head of a wearer rests against the back of a chair. Also it is desirable to provide such a pillow which will accommodate a halo and properly support the head and neck when the wearer is in either the supine or side position while sleeping.

SUMMARY OF THE INVENTION

The instant invention provides a pillow for use by the wearer of a halo head immobilizing device having a circular member and a plurality of struts. The pillow is constructed of a deformable material and has a T-shaped slot which extends between the upper and lower surfaces thereof. The leg of the T-shaped slot is adapted to extend generally parallel with the longitudinal axis of the body of a supine user. The cross bar of the T-shaped slot extends transversely to the body of a user and has a length and depth sufficient to freely accommodate the circular member of a halo without putting undue pressure thereon while the unslotted portion of the pillow bears against and supports the user's head and neck whether the user is lying on his back or his side. The leg of the T-shaped slot has sufficient length and depth to freely accommodate the support strut of the user's halo without putting undue pressure thereon.

DESCRIPTION OF THE PREFERRED EMBODIMENT

Figure 1:
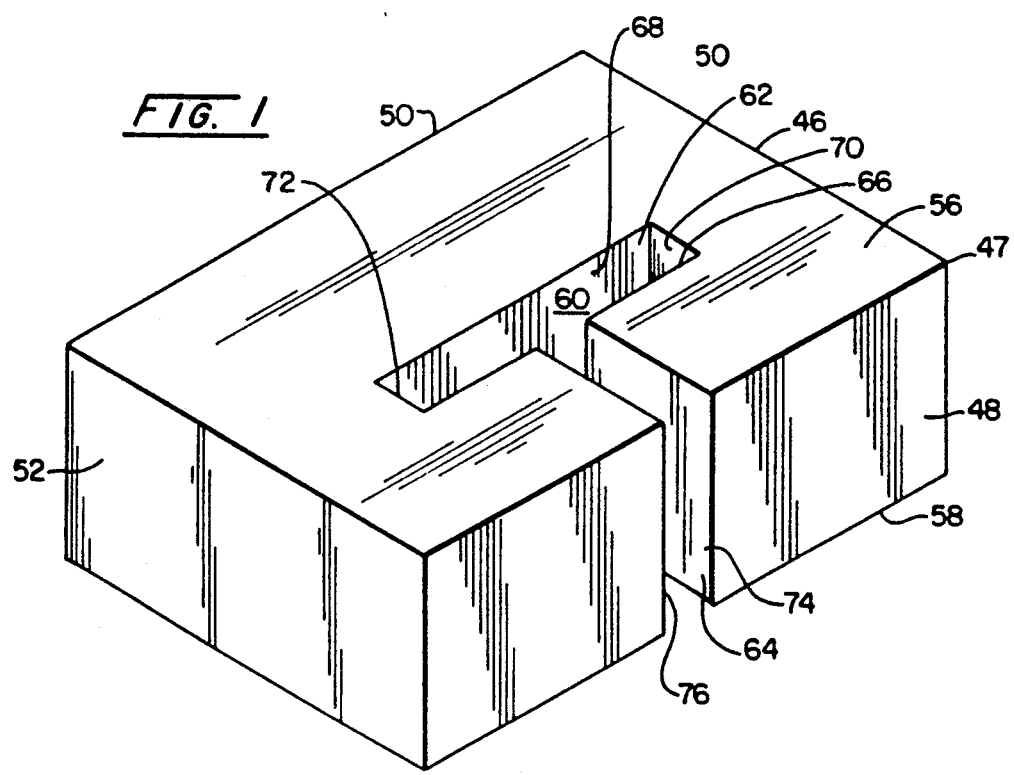
FIG. 1 is a perspective view of the halo pillow of the instant invention.
Figure 2:
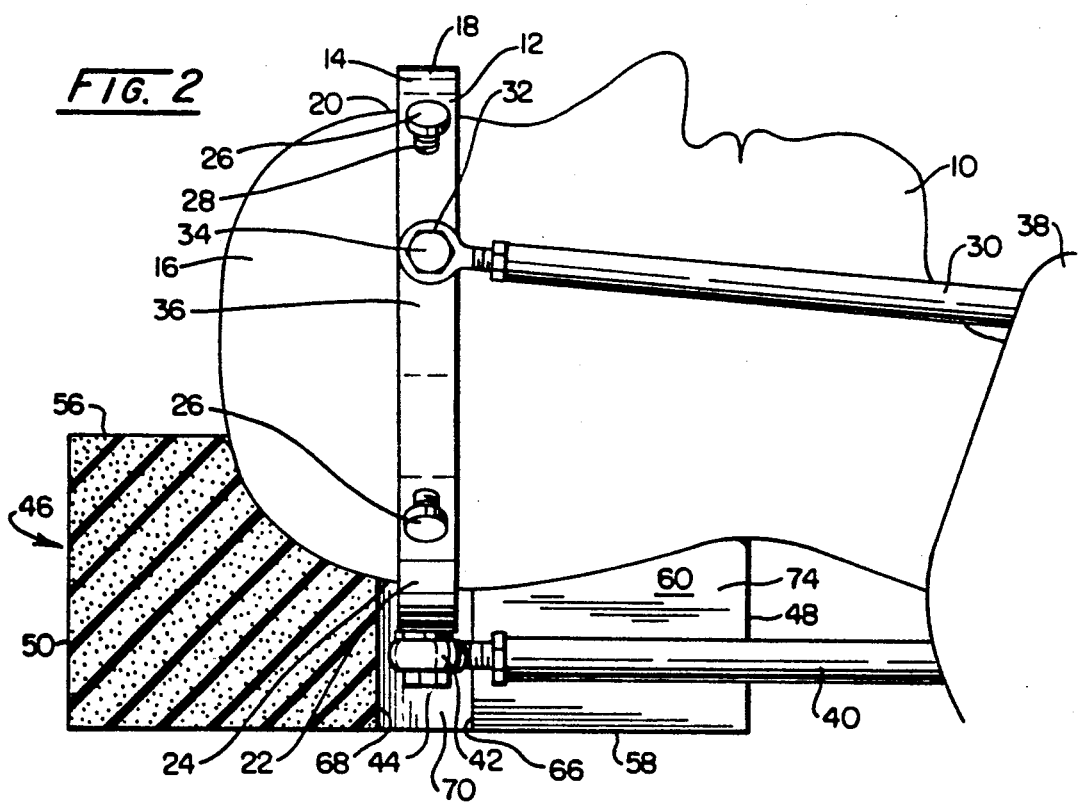
FIG. 2 is a part sectional view of the subject invention shown supporting the head of a halo wearer.

Turning to FIGS. 1 and 2, a patient (10) is shown wearing a halo head and neck immobilizing device (12). Halo device (12) includes a circular member (14) which encircles and overlies the head (16) of patient (10) such that the front portion (18) of member (14) overlies the patient's forehead (20) and the rear portion (22) of member (14) overlies the back (24) of the patient's head. A plurality of screws (26) are received in a plurality of circumferentially equally spaced threaded bores (28) formed in circular member (14) and are screwed into the first layer of the patient's skull to rigidly affix member (14) thereto.

A pair of slender rigid metallic struts (30) having an eye (32) at one end are pivotally attached to circular member (14) by threaded fasteners (34) at each side (36) thereof. The opposite ends of the struts (30), not shown, are rigidly affixed to a vest (38) worn by the patient (10). Similarly, a strut (40) identical to the struts (30) and having an eye (42) at one end thereof is affixed to the rear portion (22) of circular member (14). The opposite end of strut (40), not shown, is rigidly attached to vest (38). The struts (30 and 40) function to prevent the patient's head (16) from pivoting up and down or rotating about a longitudinal axis.

It may be observed that the struts (30 and 40) prevent a conventional pillow from supporting the head (16) of the patient (10, when the patient is in a supine position or lying on his side.

Turning to FIG. 1, it may be observed that the halo pillow (46) of the present invention is formed from a rectangular body (47) of a resilient material which may be foam rubber or other material having similar resilient qualities.

Body (47) is defined by a vertical front wall (48), a vertical rear wall (50) and a pair of vertical side walls (52 and 54). Body (47) also includes a generally flat top surface (56) and a generally flat bottom surface (58). Preferably, body (47) has a length extending between the side walls (50 and 52) of at least twenty-four inches and a width between the front and rear walls (48 and 50) respectively of at least eighteen inches. In the preferred embodiment the distance between the top and bottom surfaces (56 and 58) would be at least six inches.

It may be observed that a T-shaped slot (60) having a cross bar (62) and a leg (64) is formed within the body (47) of halo pillow (46). Cross bar (62) is defined by a vertical front wall (66), a vertical rear wall (68) and a pair of vertical end walls (70 and 72). T-shaped slot (60) extends between the top and bottom surfaces (56 and 58). Preferably cross bar (62) has a length of approximately twelve inches between end walls (70 and 72) and a width of about two inches between the front and rear walls (66 and 68). It may be observed that the leg (64) is defined by a pair of rectangular vertical side walls (74 and 76) which preferably are spaced apart a distance of approximately two inches. It has been found adequate to make the length of leg (64) this being the distance between the front wall (48) of body (47) and the front wall (66) defining cross bar (62) approximately ten inches. As mentioned previously, the thickness of pillow (46) is greater than about six inches.

Use of halo pillow (46) to support the head of a patient (10) lying in a supine position may be seen by referring to FIG. 2. In this position the rear portion (22) of circular member (14) of head and neck immobilizing device (12) resides within the cross bar (62) of the T-shaped slot (60). At the same time, rear strut (40) is received within the leg (64) of T-shaped slot (60). Thus, it may be observed that no part of the halo pillow (46) engages the halo head immobilizing device (12) when the patient's head is resting upon the pillow (46). Instead, the top surface (56) of the pillow (46) engages only the back (24) of the patient's head (16) without disturbing or touching the halo device (12) in any way. In this manner the pillow (46) supports the full weight of the patient's head (16) which reduces the weight of the head bearing down on the halo screws (26) thereby adding greatly to the patient's comfort.

It may be observed that the pillow (46) also will accommodate the patient if he chooses to lie on his side. When this occurs the circular member (14) resides within the cross bar (62) of T-shaped slot (60) and the side strut (30) resides within the leg (64) of slot (60).

Referring again to FIG. 2 it may be observed that the pillow (46) also accommodates the upper portion of a patient's neck as well as the patient's head. The distance between the front and rear walls (48 and 50) of pillow (46) may be lengthened to cause the pillow to support the entire portion of the patient's neck is so desired.

In addition to accommodating the head and neck of a patient in a supine position, pillow (46) also greatly adds to the comfort of a patient sitting in a chair having a back. In this instance the pillow (46) is interposed between the back (24) of a patient's head and the back of a chair such that the top surface (56) of the pillow engages the patient's head and the bottom surface (58) of the pillow engages the chair. Again, in this position the circular member (14) of the halo head and neck immobilizing device (12) would reside within the cross bar (62) of slot (60) and the rear strut (40) would reside within the leg (64) of slot (60). In this instance the pillow (46) would act to support the lower portion of a patient's head to thereby reduce somewhat the weight of the head supported by the screws (26) of the immobilizing device (12). This again adds to the comfort of a patient.

Since certain changes may be made in the above-described system and apparatus not departing from the scope of the invention herein and above, it is intended that all matter contained in the description or shown in the accompanying drawings shall be interpreted as illustrative and not in a limiting sense.

We claim:

1. A pillow for use by the user of a head immobilizing device known as a halo having a circular member and a plurality of longitudinally extending support struts comprising:

a unitary body of resilient material with a top surface and a bottom surface, having a T-shaped slot extending between said top and bottom surfaces thereof with the leg of the T-shaped slot being adapted to extend generally parallel with the longitudinal axis of the body of a user and defining an opening in a peripheral wall of said pillow;

the cross bar of T-shaped slot extending laterally to the longitudinal axis of the body of a user and being of a length and depth sufficient to freely accommodate the circular member of said device without putting undue pressure thereon;

the leg of said T-shaped slot being of a length and depth to freely accommodate a support strut of the device without putting undue pressure thereon; and wherein the unslotted portion of said pillow bears against and supports the user's head whether the user is lying on his back or his side.

2. The pillow of claim 1 in which said deformable material is foam rubber.

3. The pillow of claim 1 in which the leg and cross bar of said T-shaped slot have a width of at least two inches.

4. The pillow of claim 1 in which the length of the cross bar of said T-shaped slot is greater than about ten inches.

5. The pillow of claim 1 in which the length of the leg of said T-shaped slot is greater than about ten inches.

6. The pillow of claim 1 in which the depth of said pillow is greater than about six inches.

* * * * *